United States Patent [19]

Lucchetta

[11] 4,393,646
[45] Jul. 19, 1983

[54] METHOD AND APPARATUS FOR JOINING YARN OR THREAD ENDS

[75] Inventor: Sergio Lucchetta, Wädenswil, Switzerland

[73] Assignee: Maschinenfabrik Schweiter AG, Switzerland

[21] Appl. No.: 326,327

[22] Filed: Dec. 1, 1981

[30] Foreign Application Priority Data

Dec. 12, 1980 [CH] Switzerland .......................... 9216/80

[51] Int. Cl.³ .......................................... D01H 15/00
[52] U.S. Cl. ........................................................ 57/22
[58] Field of Search ...................... 57/22, 23, 261, 262, 57/263

[56] References Cited

U.S. PATENT DOCUMENTS

| | | | |
|---|---|---|---|
| 3,407,583 | 0/1968 | Irwin et al. | 57/22 |
| 3,458,905 | 8/1969 | Dodson et al. | 57/22 X |
| 3,461,661 | 0/1969 | Irwin et al. | 57/142 |
| 3,474,615 | 10/1969 | Irwin et al. | 57/22 X |
| 3,487,618 | 1/1970 | Arguelles | 57/22 |
| 4,292,796 | 10/1981 | Mima | 57/22 |

FOREIGN PATENT DOCUMENTS 495445 of 1970 Switzerland .

Primary Examiner—Donald Watkins
Attorney, Agent, or Firm—Roylance, Abrams, Berdo & Farley

[57] ABSTRACT

A splicer includes a splicing head into which the two yarn ends are introduced through an inserting slot into a turbulence chamber. The turbulence chamber is formed from two juxtaposed frustum-shaped chambers interconnected by a connecting slot. A pressure medium is tangentially introduced through one opening into each chamber for forming the splice and the flow is guided in a lemiscate-like path through the two chambers. As a result of the two oppositely directed pressure medium flows, the two yarn ends are axially centrally fixed, while the two pressure medium flows escape in the direction of the larger chamber ends and thereby subject the yarn ends to a turbulent and twisting actions, so that a joint is formed having no projecting yarn ends and no weak points due to the reduced yarn twist.

8 Claims, 4 Drawing Figures

METHOD AND APPARATUS FOR JOINING YARN OR THREAD ENDS

This invention relates to a method for joining two yarn or thread ends employing a turbulence chamber into which fluid under pressure is injected, and to a splicing head for performing this method.

BACKGROUND OF THE INVENTION

Known splicing mechanisms generally have a cylindrical channel, or in certain constructions also a slightly conical channel, into which are inserted two yarn or thread ends which are to be joined. In the axial center of the channel an air inlet is positioned tangentially with respect to the channel wall and, through that inlet, compressed air is blown into the channel so that the two yarn or thread ends are jointly subjected to turbulence. In these known mechanisms, there is the disadvantage that the tangentially entering air produces a twisting movement which is increased on the yarn or thread at one side of the splicing chamber and is decreased or completely eliminated from the other side. Due to the parallel positions of the fibers, there is then a weak point with little or no tensile strength, an apparatus of this type being shown in Swiss patent No. 495,445. In addition, the yarn or thread ends spliced in this way frequently have projecting terminal portions of the strands which are left on the threads and which, during further processing through eyelets and thread guides, can cause considerable problems.

BRIEF DESCRIPTION OF THE INVENTION

An object of the present invention is to provide an improved method for splicing two yarn or thread ends such that, while retaining a simple mechanism, splicing can be performed with a high degree of reliability and projecting ends and weak points due to reduced yarn twists are avoided.

Briefly described, the invention includes a method for splicing two yarn or thread ends in a splicing head of the type having a turbulence chamber for receiving the ends to be spliced together wherein the ends are subjected to centric pressure medium flow which is tangential to the periphery of the turbulence chamber so that the yarn or thread ends are subjected to turbulence and are twisted together to form a joint, including providing two driving pressure medium flow streams to the turbulence chamber to form the pressure medium flow therein, and guiding the two driving flow streams in opposite directions through the turbulence chamber.

In another aspect, the invention includes a splicing head for joining two yarn or thread ends, the head being of the type having a turbulence chamber therein and means for supplying fluid under pressure into the chamber, the head comprising means defining an insertion slot for inserting the yarn or thread ends into the turbulence chamber, and wherein the turbulence chamber comprises means defining first and second frusto-conical chamber portions pointing in opposite directions.

BRIEF DESCRIPTION OF THE DRAWINGS

In order that the manner in which the foregoing and other objects are attained in accordance with the invention can be understood in detail, particularly advantageous embodiments thereof will be described with reference to the accompanying drawings, which form a part of the specification, and wherein.

Figure 1:
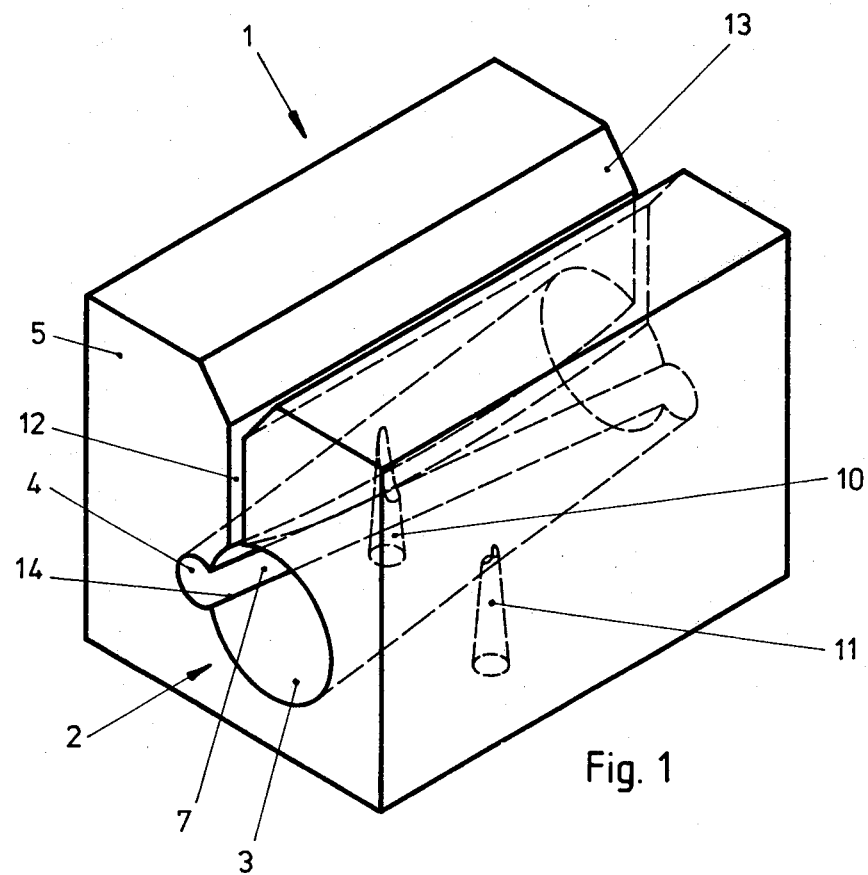
FIG. 1 is a perspective view of a thread or yarn joining head having a double chamber construction in accordance with the invention.

As will be seen in FIG. 1, the illustrated embodiment of the splicing head includes a parallelepipedic body indicated generally at 1 having end faces 5 and 6 as well as upper, lower and side surfaces. Extending through the body between end faces 5 and 6 is a turbulence chamber indicated generally at 2. The turbulence chamber is formed of two partial chamber portions 3 and 4 each of which is in the shape of a cone or a truncated cone. The cones have the same shape and are juxtaposed in such a way that they widen in opposite directions, the large end or base of one cone 3 being adjacent surface 5 and the large end of the other cone 4 being adjacent surface 6. The central axes of the cones are parallel to each other and, in the illustrated embodiment, lie in substantially the same horizontal plane. Thus, the generatrix of the two cones or truncated cones forming the contact line therebetween is located in the longitudinal plane formed by the two axes and through which extends the longitudinal section shown in FIG. 3.

In the vicinity of the contact line of the two cones forming turbulence chamber 2 is a connecting slot 7 which forms the communication connection between the two individual chambers 3 and 4. The connecting slot 7 slopes with respect to the axes of the two chambers 3, 4.

Figure 2:
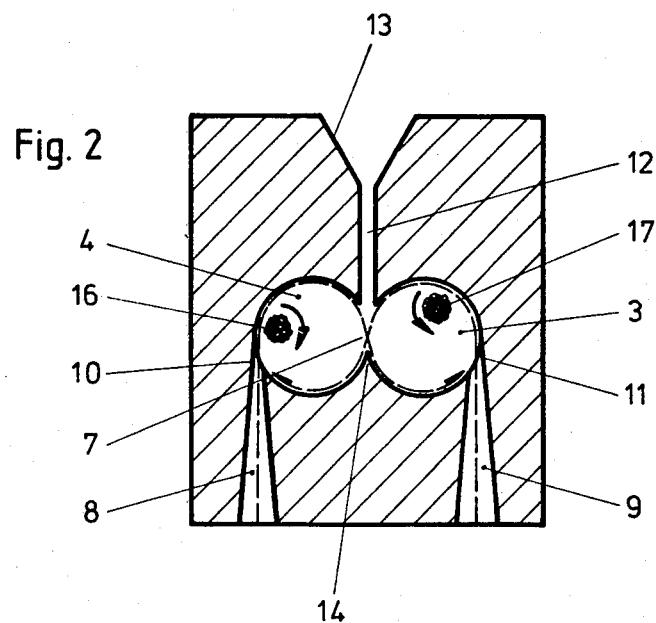
FIG. 2 is a transverse sectional view through the splicing head of FIG. 1 along line II—II of FIG. 3.
Figure 3:
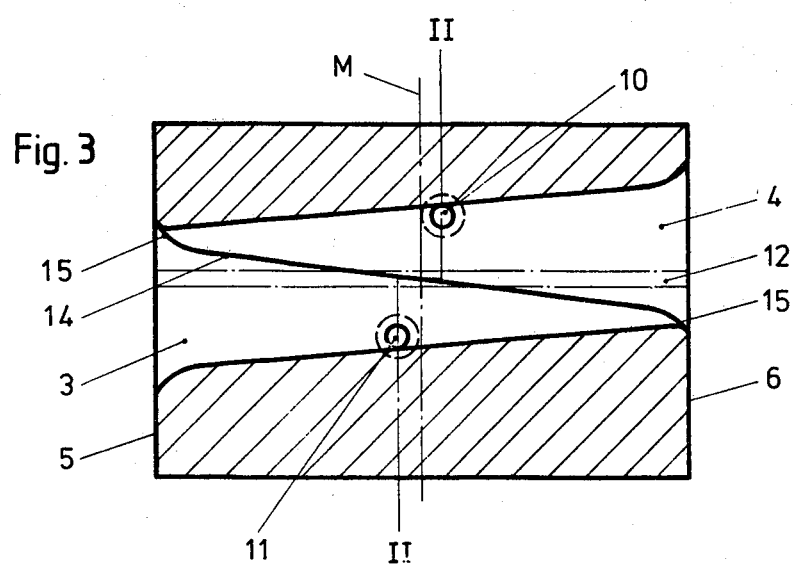
FIG. 3 is a longitudinal top plan view in section, through the splicing head of FIGS. 1 and 2.

As will be seen in FIG. 3, the section shown in FIG. 2 is perpendicular to the axes of chambers 3, 4 and is parallel to end faces 5 and 6, but is staggered as shown by lines II—II so that one partial section is located on one side of central plane M and the other section is on the other side of the central plane, so that it passes through two inlets 8 and 9 by which fluid pressure medium is supplied to turbulence chamber 2.

The pressure medium connection 8, 9 terminates in openings 10, 11 at chambers 3 and 4, respectively, the openings being positioned so that they enter chamber portions 3 and 4 tangentially. Also as will be seen in FIG. 3, the openings 10, 11, are slightly axially displaced or offset from each other, one opening 10 being located closer to surface 6 and opening 11 being closer to surface 5 on opposite sides of central plane M.

The positions of pressure medium connections 8, 9 can also differ from the positions shown in FIG. 2 wherein the axes of openings 10, 11 of connections 8, 9 are parallel to one another. In other words, opening 10, 11 can be positioned at other points on the peripheries of chambers 3 and 4. However, the displaced position of openings 10, 11 with respect to central plane M must always be maintained because, otherwise, the pressure medium flow streams entering and circulating in chambers 3, 4 would have a mutually interfering or disturbing action, even though they enter into different chambers, as will be recognized from the following discussion.

As will be understood from FIGS. 1 and 2, splicing head 1 has an inserting slot 12 extending inwardly from the top of head 1 along the entire length of chamber 2 which serves for the insertion of the thread ends to be spliced. To permit easier insertion of the thread ends, the upper opening of slot 12 is chamfered as shown at 13. Insertion slot 12 only passes directly over connecting slot 7 in central plane M. FIG. 3 shows, by means of dot-dash lines, the relative positions of insertion slot 12 with respect to the central plane and it will be apparent therefrom that slot 12 communicates on one side of plane M with chamber 3 and on the other side with chamber 4. As a result, on inserting two yarn or thread ends to be spliced, one end is guided into chamber 3 and the other into chamber 4. The edge 14 formed at connecting slot 7 is inclined with respect to insertion slot 12, as seen in FIG. 3. Also as seen in FIG. 3, the ends of chamber portions 3, 4 at their larger ends where they open at end faces 5, 6 of splicing head 1 are appropriately provided with rounded portions 15.

Figure 4:
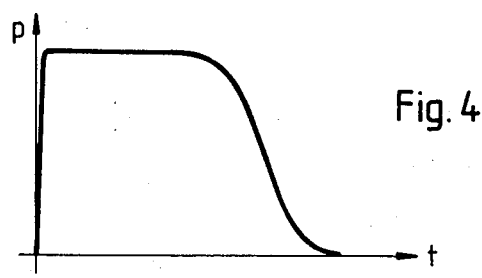
FIG. 4 is a pressure-time diagram showing the inlet flow pressure distribution as a function of time.

Two yarn or thread ends are joined in the splicing head 1 in the following manner. The two ends, pointing in opposite directions, are inserted through inserting slot 12 and cut off in the vicinity of end faces 5, 6. Due to the slope of edge 14 with respect to slot 12, one end is located in one chamber and the other end in the other chamber. Pressure medium flow is now produced in chamber portions 3, 4 through pressure medium connections 8, 9. As illustrated in FIG. 4, pressure medium flow is produced in the form of sudden bursts. The pressure energy rise reaches its maximum value after a very short time, remains constant during the splicing time, and then drops to zero again after interruption of the pressure medium supply.

It will be apparent from FIG. 2 that in chamber portions 3 and 4 the pressure medium flow is guided in the form of a horizontal figure eight, or a lemniscate. The pressure medium flow entering a chamber flows to edge 14 whereupon it passes into the other chamber, flows through the latter around the periphery thereof and, at edge 14, flows back into the first chamber. This process can be repeated a number of times as the flow moves in the direction of the end faces 5, 6 of the splicing head, the flow in each chamber portion being along a generally helical path in the direction of the larger end thereof. The yarn or thread ends are subjected to a turbulent action and are spliced together. As a result of the sudden action of the pressure medium flow, the two ends are fixed at plane M of the splicing head 1 while the two pressure medium flows necessarily travel in the direction of the winding chambers 3, 4. In accordance with the lemniscate flow guidance, the yarn or thread ends are moved in a corresponding manner and are subjected to turbulence and twisting. The result is a splice having no projecting yarn or thread ends and no weak point due to reduced yarn twist.

Obviously, the connecting slot 7 must be designed in such a way that the outlet tangent of one chamber 3, 4 at the slot is aligned with the inlet tangent of the other chamber 4, 3 so that the pressure medium flow passes in a substantially loss-free manner from one chamber portion into the other.

In FIG. 2, the yarn ends are identified as 16 and 17, and the arrows indicate the rotation direction. However, the yarn ends 16, 17 do not occupy a stationary position. Rather, during the maintenance of the pressure medium flow there is an intense processing of yarn end 16, 17, during which they rotate about the axes of the conical chamber portions. Due to the two juxtaposed pressure medium flow which are directed in opposite directions, the thread ends are secured in the vicinity of the central plane M of splicing head 1 while the remaining portions are subject to a turbulent and twisting action.

For inserting the yarn or thread ends in splicing head 1, the same means are used as are employed in knotting devices on automatic spooling or winding machines, such devices being known, for example, from German Auslegeschrift No. 1,256,571. It is merely necessary to cut off the yarn or thread ends 16, 17 before carrying out the splicing process. The splicing process shortens the yarn or thread ends 16, 17 so that projecting yarn ends are reliably avoided.

Splicing head 1 can be appropriately be formed from an abrasion-resistant material such as steel, a non-ferrous metal or a plastic material.

While certain advantageous embodiments have been chosen to illustrate the invention it will be understood by those skilled in the art that various changes and modifications can be made therein without departing from the scope of the invention as defined in the appended claims.

What is claimed is:

1. A method for splicing two yarn or thread ends in a splicing head of the type having a turbulence chamber for receiving the ends to be spliced together wherein the ends are subjected to centric pressure medium flow which is tangential to the periphery of the turbulence chamber so that the yarn or thread ends are subjected to turbulence and are twisted together to form a joint, including
    providing two driving pressure medium flow streams to the turbulence chamber to form the pressure medium flow therein,
    introducing the two driving flow streams into the turbulence chamber through inlets at opposite side walls thereof, the two streams at the inlets being parallel with each other, and
    guiding the two driving flow streams in opposite directions along lemniscate-like paths through the turbulence chamber.

2. A splicing head for joining two yarn or thread ends, the head being of the type having a turbulence chamber therein and means for supplying fluid under pressure into the chamber, the head comprising
    means defining an insertion slot for inserting the yarn or thread ends into the turbulence chamber,
    and wherein the turbulence chamber comprises
    means defining first and second frusto-conical chamber portions pointing in opposite directions.

3. A splicing head according to claim 2 wherein the axes of said chamber portions are parallel with each other,
    said chamber portions opening into each other along a slot formed in the contacting region of their generatrices, said slot being inclined relative to said axes.

4. A splicing head according to claim 3 wherein said means for supplying fluid under pressure includes
    means defining inlet openings to said turbulence chamber at opposite sides thereof, said inlet openings being formed to deliver fluid tangentially into said chamber.

5. A splicing head according to claim 4 wherein said openings are located adjacent walls opposite said slot in each of said chamber portions.

6. A splicing head according to claim 2 wherein said means for supplying fluid under pressure includes
    means defining inlet openings to said turbulence chamber at opposite sides thereof, said inlet openings being formed to deliver fluid tangentially into said chamber.

7. A splicing head according to claim 2 wherein said means defining said chamber portions includes rounded edge portions at the base of each of said chamber portions.

8. A method for splicing two yarn or thread ends in a splicing head of the type having a turbulence chamber for receiving the ends to be spliced together wherein the ends are treated by a centric pressure medium flow comprising at least two partial flows such that the ends are subjected to turbulence and are twisted together to form a joint, including provﾠiding a turbulence chamber which includes two adjoining, partially separated chamber portions, introducing one of the partial flows tangentially into one end of the chamber portions and the other partial flow tangentially into the other chamber portion, and guiding each of the partial flows along a generally lemniscate-like path from one chamber portion to the other so that the flows along the paths are in the same circular directions in each chamber portion.

* * * * *